United States Patent [19]
Duplantier et al.

[11] Patent Number: 6,004,974
[45] Date of Patent: Dec. 21, 1999

[54] TRICYCLIC 5,6-DIHYDRO-9H-PYRAZOLO[3,4-C]-1,2,4-TRIAZOLO[4,3-α]PYRIDINES

[75] Inventors: Allen J. Duplantier, Ledyard; Kelvin Cooper, Noank, both of Conn.

[73] Assignee: Pfizer Inc, New York, N.Y.

[21] Appl. No.: 08/973,590

[22] PCT Filed: Jun. 6, 1995

[86] PCT No.: PCT/IB95/00429

§ 371 Date: Mar. 27, 1998

§ 102(e) Date: Mar. 27, 1998

[87] PCT Pub. No.: WO96/39408

PCT Pub. Date: Dec. 12, 1996

[51] Int. Cl.$^6$ .......................... A61K 31/44; C07D 471/12
[52] U.S. Cl. ................................ 514/293; 546/82
[58] Field of Search ................ 546/82; 514/293

[56] References Cited

U.S. PATENT DOCUMENTS 3,697,532 10/1972 Hoehn ........................ 260/295.5 T
5,545,647 8/1996 Tanaka ........................ 514/343

OTHER PUBLICATIONS

Nicholson CD et al. TIPS. 12, 19–27, Jan. 1991.

*Primary Examiner*—Evelyn Mei Huang
*Attorney, Agent, or Firm*—Peter C. Richardson; Paul H. Ginsburg; Raymond M. Speer

[57] ABSTRACT

A compound of the formula

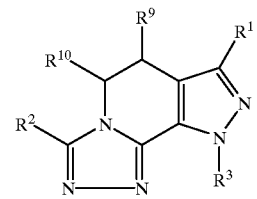

wherein $R^1$, $R^2$, $R^3$, $R^9$ and $R^{10}$ are as defined above The compound of formula I and the pharmaceutically acceptable salts thereof are useful in inhibiting phosphodiesterase (PDE) type IV and the production of tumor necrosis factor (TNF) and in the treatment of asthma, arthritis, bronchitis, chronic obstructive airways disease, psoriasis, allergic rhinitis, dermatitis and other inflammatory diseases characterized by phosphodiesterase (PDE) Type IV activity as well as AIDS, sepsis, septic shock and other diseases, such as cachexia, involving the production of TNF.

7 Claims, No Drawings

TRICYCLIC 5,6-DIHYDRO-9H-PYRAZOLO[3,4-C]-1,2,4-TRIAZOLO[4,3-α]PYRIDINES

This application is the national phase of PCT/IB95/00429, filed on Jun. 6, 1995, published as WO 96/39408 on Dec. 12, 1996.

BACKGROUND OF THE INVENTION

This invention relates to tricyclic 5,6-dihydro-9H-pyrazolo[3,4-c]-1,2,4-triazolo[4,3-α]pyridines which are selective inhibitors of phosphodiesterase (PDE) type IV or the production of tumor necrosis factor (TNF) and as such are useful in the treatment of asthma, arthritis, bronchitis, chronic obstructive airways disease, psoriasis, allergic rhinitis, dermatitis and other inflammatory diseases as well as AIDS, sepsis, septic shock and other diseases, such as cachexia, involving the production of TNF. Compounds of the present invention may have combined PDE IV and TNF inhibitory activity.

This invention also relates to a method of using such compounds in the treatment of the above diseases in mammals, especially humans and to pharmaceutical compositions useful therefor.

Since the recognition that cyclic AMP is an intracellular second messenger (E. W. Sutherland, and T. W. Rall, *Pharmacol. Rev.*, 1960, 12, 265), inhibition of the phosphodiesterases has been a target for modulation and, accordingly, therapeutic intervention in a range of disease processes. More recently, distinct classes of PDE have been recognized (J. A. Beavo and D. H. Reifsnyder, *TiPS*, 1990, 11, 150), and their selective inhibition has led to improved drug therapy (C. D. Nicholson, R. A. Challiss and M. Shahid, *TiPS*, 1991, 12, 19). More particularly, it has been recognized that inhibition of PDE type IV can lead to inhibition of inflammatory mediator release (M. W. Verghese et al., *J. Mol. Cell Cardiol.*, 1989, 12 (Suppl. II), S 61) and airway smooth muscle relaxation (T. J. Torphy in *Directions for New Anti-Asthma Drugs*, eds S. R. O'Donnell and C. G. A. Persson, 1988, 37, Birkhauser-Verlag). Thus, compounds that inhibit PDE type IV, but which have poor activity against other PDE types, inhibit the release of inflammatory mediators and relax airway smooth muscle without causing cardiovascular effects or antiplatelet effects.

TNF is recognized to be involved in many infectious and auto-immune diseases, including cachexia (W. Friers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62, S11).

SUMMARY OF THE INVENTION

The present invention relates to a compound of the formula

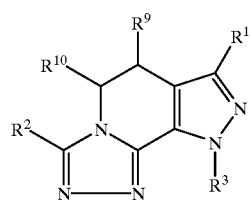

I and the pharmaceutically acceptable salts thereof; wherein
$R^1$ is hydrogen, $(C_1-C_6)$alkyl, $(C_1-C_6)$alkoxy, $(C_2-C_4)$alkenyl, phenyl, dimethylamino, $(C_3-C_6)$cycloalkyl, $(C_3-C_6)$cycloalkyl $(C_1-C_3)$alkyl or $(C_1-C_6)$acyl wherein the alkyl, phenyl or alkenyl groups may be substituted with up to two hydroxy, $(C_1-C_3)$alkyl, or trifluoromethyl groups, or up to three halogens;

$R^2$ and $R^3$ are each independently selected from the group consisting of hydrogen, $(C_1-C_{14})$alkyl, $(C_1-C_7)$alkoxy $(C_1-C_7)$alkyl, $(C_2-C_{14})$alkenyl, $(C_3-C_7)$cycloalkyl, $(C_3-C_7)$cycloalkyl$(C_1-C_2)$alkyl, a saturated or unsaturated $(C_4-C_7)$ heterocyclic$(CH_2)_n$ group wherein n is 0, 1 or 2, containing as the heteroatom one or two of the group consisting of oxygen, sulphur, sulphonyl, nitrogen and $NR^4$ wherein $R^4$ is hydrogen or $(C_1-C_4)$alkyl; or a group of the formula

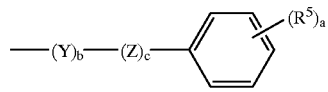

II wherein a is an integer from 1 to 5; b and c are 0 or 1; $R^5$ is hydrogen, hydroxy, $(C_1-C_5)$alkyl, $(C_2-C_5)$alkenyl, $(C_1-C_5)$alkoxy, $(C_3-C_6)$cycloalkoxy, halogen, trifluoromethyl, $CO_2R^6$, $CONR^6R^7$, $NR^6R^7$, $NO_2$ or $SO_2NR^6R^7$ wherein $R^8$ and $R^7$ are each independently hydrogen or $(C_1-C_4)$alkyl; wherein Z is oxygen, sulphur, $SO_2$, CO or $NR^8$ wherein $R^8$ is hydrogen or $(C_1-C_4)$alkyl; and Y is $(C_1-C_5)$alkylene or $(C_2-C_6)$alkenyl optionally substituted with up to two $(C_1-C_7)$alkyl or $(C_3-C_7)$ cycloalkyl groups; wherein each of the alkyl, alkenyl, cycloalkyl, alkoxyalkyl or heterocyclic groups may be substituted with one to fourteen, preferably one to five, of the group consisting of $(C_1-C_2)$alkyl, trifluoromethyl or halogen; and $R^9$ and $R^{10}$ are each independently selected from the group consisting of hydrogen, $(C_1-C_6)$alkyl, $(C_1-C_6)$alkoxy, $(C_6-C_{10})$aryl and $(C_6-C_{10})$aryloxy.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "thenyl", as used herein, unless otherwise indicated, is defined by thiophene-$CH_2$—.

The term "aryl", as used herein, unless otherwise indicated, includes an organic radical derived from an aromatic hydrocarbon by removal of one hydrogen, such as phenyl or naphthyl, optionally substituted by 1 to 3 substituents independently selected from the group consisting of fluoro, chloro, cyano, nitro, trifluoromethyl, $(C_1-C_6)$alkoxy, $(C_6-C_{10})$aryloxy, trifluoromethoxy, difluoromethoxy and $(C_1-C_6)$alkyl.

The term "aryloxy", as used herein, includes O-aryl groups wherein "aryl" is defined above.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

Preferred compounds of formula I include those wherein $R^1$ is methyl, ethyl or isopropyl.

Other preferred compounds of formula I include those wherein $R^3$ is $(C_1-C_6)$alkyl, $(C_2-C_6)$alkenyl, $(C_3-C_7)$ cycloalkyl, $(C_3-C_7)$cycloalkyl$(C_1-C_6)$alkyl or phenyl optionally substituted with 1 or 2 of the group consisting of hydrogen, hydroxy, $(C_1-C_5)$alkyl, $(C_2-C_5)$alkenyl, $(C_1-C_5)$ alkoxy, halogen, trifluoromethyl, $CO_2R^6$, $CONR^6R^7$, $NR^6R^7$, $NO_2$ or $SO_2NR^6R^7$ wherein $R^6$ and $R^7$ are each independently hydrogen or $(C_1-C_4)$alkyl.

Specific preferred compounds of formula I include the following:

9-cyclopentyl-5,6-dihydro-7-ethyl-3-9H-pyrazolo[3,4-c]-1,2,4-triazolo[4,3-α]pyridine;

9-cyclopentyl-5,6-dihydro-7-ethyl-3-(furan-2-yl)-9H-pyrazolo[3,4-c]-1,2,4-triazolo[4,3-α]pyridine;

9-cyclopentyl-5,6-dihydro-7-ethyl-3-(2-pyridyl)-9H-pyrazolo[3,4-c]-1,2,4-triazolo[4,3-α]pyridine;

9-cyclopentyl-5,6-dihydro-7-ethyl-3-(4-pyridyl)-9H-pyrazolo[3,4-c]-1,2,4-triazolo[4,3-α]pyridine;

9-cyclopentyl-5,6-dihydro-7-ethyl-3-(3-thenyl)-9H-pyrazolo[3,4-c]-1,2,4-triazolo[4,3-α]pyridine;

3-benzyl-9-cyclopentyl-5,6-dihydro-7-ethyl-9H-pyrazolo[3,4-c]-1,2,4-triazolo[4,3-α]pyridine;

9-cyclopentyl-5,6-dihydro-7-ethyl-3-propyl-9H-pyrazolo[3,4-]-1,2,4-triazolo[4,3-α]pyridine;

3,9-dicyclopentyl-5,6-dihydro-7-ethyl-9H-pyrazolo[3,4-c]-1,2,4-triazolo [4,3-α]pyridine;

9-cyclopentyl-5,6-dihydro-7-ethyl-3-(1-methylcyclohex-1-yl)-9H-pyrazolo[3,4-c]-1,2,4-triazolo[4,3-α] pyridine;

3-(tert-butyl)-9-cyclopentyl-5,6-dihydro-7-ethyl-9H-pyrazolo[3,4-c]-triazolo[4,3-α]pyridine;

9-cyclopentyl-5,6-dihydro-7-ethyl-3-(2-methylphenyl)-9H-pyrazolo[3,4-c]-1,2,4-triazolo[4,3-α]pyridine;

9-cyclopentyl-5,6-dihydro-7-ethyl-3-(2-methoxyphenyl)-9H-pyrazolo[3,4-c]-1,2,4-triazolo[4,3-α]pyridine;

9-cyclopentyl-5,6-dihydro-7-ethyl-3-(thien-2-yl)-9H-pyrazolo[3,4-c]1,2,4-triazolo[4,3-α]pyridine;

3-(2-chlorophenyl)-9-cyclopentyl-5,6-dihydro-7-ethyl-9H-pyrazolo[3,4-c]-1,2,4-triazolo[4,3-α]pyridine;

9-cyclopentyl-5,6-dihydro-7-ethyl-3-(2-iodophenyl)-9H-pyrazolo[3,4-c]-1,2,4-triazolo[4,3-α]pyridine;

9-cyclopentyl-5,6-dihydro-7-ethyl-3-(2-trifluoromethylphenyl)-9H-pyrazolo[3,4-c]-1,2,4-triazolo[4,3-α]pyridine; and 5,6-dihydro-7-ethyl-9-(4-fluorophenyl)-3-(1-methylcyclohex-1-yl)-9H-pyrazolo[3,4-c]-1,2,4-triazolo[4,3-α]pyridine.

The present invention also relates to a method for the inhibition of phosphodiesterase (PDE) type IV and the production of TNF comprising administering to a patient an effective amount of a compound according to formula I or a pharmaceutically acceptable salt thereof.

The present invention also relates to a method of treating an inflammatory condition in mammals which comprises administering to said mammal an antiinflammatory amount of a compound of the formula I or a pharmaceutically acceptable salt thereof.

The present invention also relates to a pharmaceutical composition for the (a) treatment of asthma, arthritis, bronchitis, chronic obstructive airways disease, psoriasis, allergic rhinitis, dermatitis and other inflammatory diseases characterized by phosphodiesterase (PDE) Type IV activity, AIDS, sepsis, septic shock and other diseases, such as cachexia, involving the production of TNF, or (b) the inhibition of phosphodiesterase (PDE) type IV and the production of TNF comprising an effective amount of a compound according to formula I or a pharmaceutically acceptable salts thereof together with a pharmaceutically acceptable carrier.

This invention also relates to a method of treating or preventing a condition selected from the group consisting of asthma, arthritis, bronchitis, chronic obstructive airways disease, psoriasis, allergic rhinitis, dermatitis and other inflammatory diseases, AIDS, septic shock and other diseases, such as cachexia, involving the production of TNF comprising administering to a patient an effective amount of a compound according to formula I or a pharmaceutically acceptable salt thereof.

DETAILED DESCRIPTION OF THE INVENTION

The following reaction schemes illustrate, but are not limiting to, the preparation of the compounds of the present Invention. Unless otherwise indicated $R^1$, $R^2$, $R^3$, $R^9$ and $R^{10}$ in the reaction schemes and the discussion that follow are defined as above.

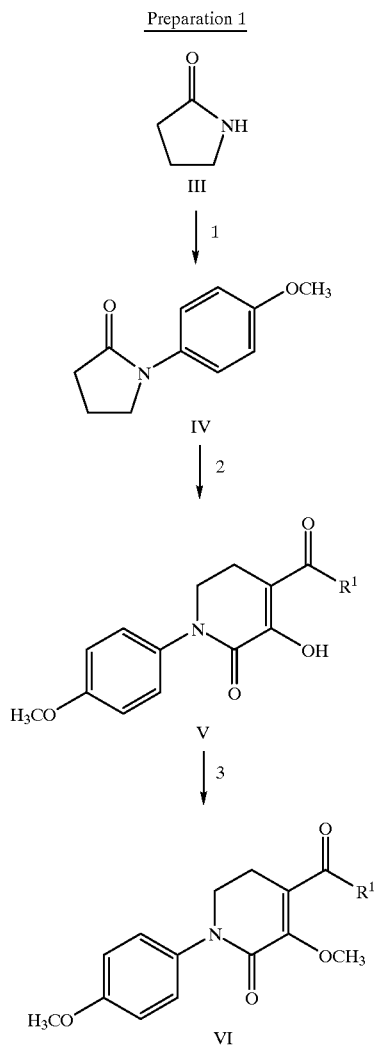

Preparation 1

5
Preparation 2
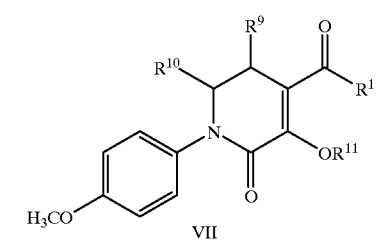
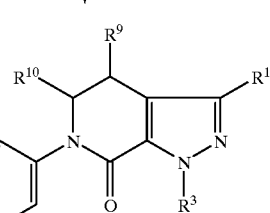
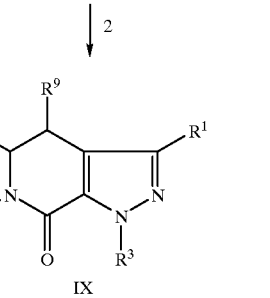
Preparation 3
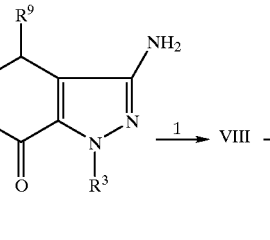
Preparation 4
XII →¹→  →²→
VIII →³→ IX
6
Scheme 1
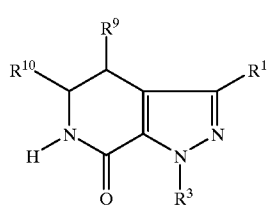
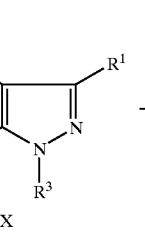 →²→ I
Scheme 2
X →¹→ 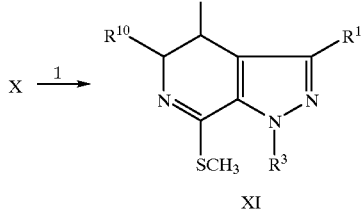 →²→ I
Scheme 3
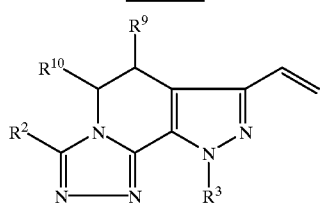
↓ 1
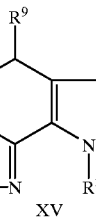
↓ 2

-continued

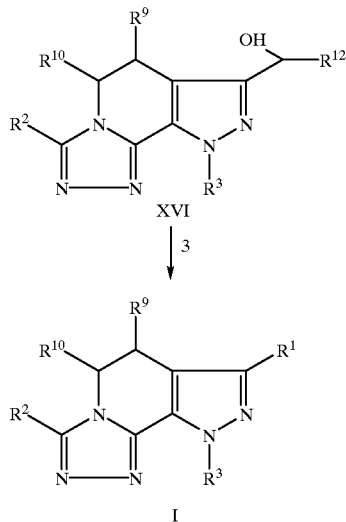

XVI

↓ 3

I

In Reaction 1 of Preparation 1, the 2-pyrrolidinone compound of formula III is converted to the corresponding N-(4-methoxyphenyl)-2-pyrrolidone compound of formula IV by reacting III with 4-iodoanisole or 4-bromoanisole neat in the presence of copper power and potassium carbonate. The reaction mixture is heated to a temperature between about 110° C. to about 170° C., preferably about 150° C., for a time period between about 14 hours to about 22 hours, preferably about 18 hours, under inert reaction conditions.

In Reaction 2 of Preparation 1, $R^1$ halide, wherein $R^1$ is $(C_1–C_6)$alkyl, is added to a suspension of magnesium in an anhydrous aprotic solvent. The reaction mixture is heated to reflux until all the magnesium is consumed and thereafter cooled to a temperature between about −15° C. to about 15° C., preferably about 0° C. The N-(4-methoxyphenyl)-2-pyrrolidone compound of formula IV is then added and the reaction mixture is warmed to room temperature while being stirred for a time period between about 1.5 hours to about 2.5 hours, preferably about 2 hours. Suitable alkyl halides include bromomethane, bromoethane or bromopropane. The preferred anhydrous aprotic solvent is anhydrous ether.

The desired intermediate is isolated and converted to the corresponding 1,2,5,6-tetrahydropyridine compound of formula V by dispersing the precipitate in a mixture of a non-polar aprotic solvent and base. Ethyl oxalyl chloride is added and the reaction mixture is heated to reflux for a time period between about 1.5 hours to about 4.5 hours, preferably about 3.0 hours. The preferred non-polar aprotic solvent is benzene and the preferred base is sodium hydroxide. The solvents are removed and the resulting residue is treated with a solution of sodium alkoxide in ethanol. After heating at reflux for a time period between about 1 hour and about 3 hours, preferably about 1.5 hours, the mixture is concentrated under reduced pressure and acidified to a pH of about 3 with hydrochloric acid.

In Reaction 3 of Preparation 1, the compound of formula V is converted to the corresponding 3-methoxy-1,2,5,6-tetrahydropyridine compound of formula VI by heating to reflux a reaction mixture of V and 3-methyl-1-p-tolyltriazene in an aprotic solvent, preferably 1,2-dichloroethane, for a time period between about 30 minutes to about 2 hours, preferably about 45 minutes.

In Reaction 1 of Preparation 2, the 1,2,5,6-tetrahydropyridine compound of formula VII, wherein $R^{11}$ is hydrogen or methyl, is converted to the corresponding 4,5,6,7-tetrahydro-7-oxo-1H-pyrazolo[3,4-c]pyridine compound of formula VIII by reacting VII with a hydrazine compound of the formula $R^3HNNH_2$, wherein $R^3$ is as defined above. Both derivatives of the compound of formula VII, 3-hydroxy and 3-methoxy, may be used as starting materials under one of three different sets of reaction conditions.

Under one set of reaction conditions, the 1,2,5,6-tetrahydropyridine compound of formula VII is converted to the corresponding compound of formula VII by reacting VII with a hydrazine hydrochloride and sodium alkoxide in an anhydrous polar protic solvent. The preferred sodium alkoxide is sodium methoxide and the preferred anhydrous polar protic solvent is anhydrous ethanol. The reaction mixture is heated to reflux for a Ume period between about 9 hours to about 15 hours, preferably about 12 hours.

Under a second set of reaction conditions, the 1,2,5,6-tetrahydropyridine compound VII is converted to the corresponding compound of formula VIII by reacting VII with a hydrazine in an anhydrous polar protic solvent, preferably ethanol. The reaction mixture is heated to reflux for a time period between about 16 hours to about 24 hours, preferably about 20 hours.

Under a third set of reaction conditions, the 1,2,5,6-tetrahydropyridine compound of formula VII is converted to the corresponding compound of formula VIII by reacting VII with either a hydrazine or hydrazine hydrochloride in a polar protic solvent, preferably methanol. The reaction mixture is heated to a temperature between about 70° C. to about 110° C., preferably about 90° C., under a gentle stream of nitrogen until all of the solvent is removed. The neat mixture is then heated to a temperature between about 120° C. to about 180° C., preferably about 1500C, for a time period between about 30 minutes to about 90 minutes, preferably 60 minutes.

In Reaction 2 of Preparation 2, the compound of formula VII is converted to the corresponding 6-H-4,5,6,7-tetrahydro-7-oxo-1H-pyrazolo[3,4-c]pyridine compound of formula IX by reacting a solution of VIII in a polar aprotic solvent, preferably acetonitrile, with a solution of cerium (IV) ammonium nitrate in water at a temperature between about −15° C. to about 15° C., preferably about 0° C., for a time period between about 20 minutes to about 50 minutes, preferably about 35 minutes. Upon completion of the reaction, the mixture is diluted with water and extracted with ethyl acetate. The combined organics are then washed with saturated sodium bicarbonate followed by sodium sulfite.

In Reaction 1 of Preparation 3, the compound of formula XII, prepared as described in U.S. Pat. No. 3,423,414, is converted to the corresponding compound of formula VIII, wherein $R^1$ is dimethylamino, by treating XII with sodium hydride in a polar aprotic solvent, such as tetrahydrofuran, at a temperature between about 0° C. to about 62° C., preferably about 25° C., for a time period between about 1 hour to about 6 hours, preferably about 1 hour. An excess amount of methyl iodide is then added to the reaction mixture at room temperature and the reaction mixture is allowed to stir for a time period between about 1 hour to about 24 hours, preferably about 2 hours.

In Reaction 2 of Preparation 3, the compound of formula VIII is further reacted to give the corresponding 6-H-4,5,6,7-tetrahydro-7-oxo-1H-pyrazolo[3,4c-]pyridine compound of formula IX, wherein $R^1$ is dialkylamino, according to the procedure described above in Reaction 2 of Preparation 2.

In Reaction 1 of Preparation 4, the compound of formula XII is converted to the corresponding compound of formula XII by reacting XII with bromotrimethylsilane and sodium nitrite in an aprotic solvent, such as carbon tetrachloride, at a temperature between about 0° C. to about 25° C., preferably about 25° C., for a time period between about 6 hours to about 48 hours, preferably about 24 hours.

In Reaction 2 of Preparation 4, the compound of formula XIII is converted to the corresponding compound of formula VII, wherein $R^1$ is vinyl, by reacting XIII with vinyltributyltin and a catalytic amount of tetrakis(triphenylphosphine) palladium(O) in a non-polar aprotic solvent, such as benzene, at a temperature between about 80° C. to about 120° C., preferably about 100° C., for a time period between about 24 hours to about 72 hours, preferably about 48 hours.

In Reaction 3 of Preparation 3, the compound of formula VIII is further reacted to give the corresponding 6-H4,5,6, 7-tetrahydro-7-oxo-1 H-pyrazolo[3,4-c]pyridine compound of formula IX, wherein $R^1$ is alkenyl, according to the procedure described above in Reaction 2 of Preparation 2.

In Reaction 1 of Scheme 1, the lactam compound of formula IX is converted to the corresponding thiolactam compound of formula X by reacting IX with phosphorus pentasulfide in a polar aprotic solvent, such as 1,4-dioxane or pyridine. The reaction mixture is heated to reflux for a time period between about 12 hours to about 48 hours, preferably about 18 hours.

In Reaction 2 of Scheme 1, the thiolactam X is converted to the corresponding tricyclic 5,6-dihydro-9H-pyrazolo[3,4-c]-1,2,4triazolo[4,3α-]pyridine compound of formula I by treating X with anhydrous hydrazine in the presence of an anhydrous aprotic solvent, such as pyridine, under inert reaction conditions. The reaction mixture is heated to a temperature between about 50° C. to about 100° C., preferably about 70° C., for a time period between about 5 minutes to about 30 minutes, preferably about 5 minutes. The volatile materials are then removed under reduced pressure and fresh anhydrous aprotic solvent, preferably pyridine, is added followed by the addition of an appropriate acid chloride of the formula $R^2COCl$, wherein $R^2$ is as defined above. The resulting reaction mixture is stirred for a time period between about 1 hour to about 4 hours, preferably about 2 hours. The volatile materials are once again removed under reduced pressure. The residue is dissolved in an aprotic solvent, such as dimethylformamide, and heated to reflux for a time period between about 1 hour to about 4 hours, preferably about 2 hours.

In Reaction 1 of Scheme 2, the thiolactam compound of formula X is converted to the corresponding methylthio compound of formula XI by treating a mixture of X and silica gel in an aprotic solvent, such as ether, with a solution of diazomethane in ether. The reaction temperature will generally be in the range of about −5° C. to about 10° C., preferably about 0° C., for a time period between about 30 minutes to about 5 hours, preferably about 1 hour.

In Reaction 2 of Scheme 2, the methylthiol compound of formula XI is converted to the corresponding tricyclic 5,6-dihydro-9H-pyrazolo[3,4-c]-1,2,4-triazolo[4,3-a] pyridine compound of formula I by reacting XI with a hydrazide compound of the formula $R^2CONHNH_2$, or the corresponding hydrochloride salt form, in an aprotic solvent, such as pyridine, under inert reaction conditions. The reaction mixture is heated to a temperature between about 120° C. to about 150° C., preferably about 135° C., for a time period between about 2 hours to about 6 hours, preferably about 4 hours. The volatile materials are then removed under reduced pressure and the resulting oil is heated further to a temperature between about 135° C. to about 165° C., preferably about 150° C., for a time period between about 2 hours to about 6 hours, preferably about 4 hours.

In Reaction 1 of Scheme 3, the compound of formula XIV is converted to the corresponding compound of formula XV according to the procedure described In Canadian Journal of Chemistry, 33, 1714 (1955).

In Reaction 2 of Scheme 3, the compound of formula XV is converted to the corresponding compound of formula XVI, wherein $R^{12}$ is $(C_1-C_6)$alkyl, by reacting XV with alkyl lithium in a polar aprotic solvent, such as ether, at a temperature between about −50° C. to about −80° C., preferably about −78° C., for a time period between about 15 minutes to about 2 hours, preferably about 30 minutes.

In Reaction 3 of Scheme 3, the compound of formula XVI is converted to the corresponding 5,6-dihydro-9H-pyrazolo [3,4-c]-1,2,4-triazolo[4,3-a]pyridine compound of formula I, wherein $R^1$ is $(C_1-C_6)$acyl, by treating XVI with pyridinium chlorochromate in a non-polar aprotic solvent, such as methylene chloride, at room temperature for a time period between about 6 hours to about 24 hours, preferably about 12 hours.

The ability of the compounds or the pharmaceutically acceptable salts thereof to inhibit phosphodiesterase IV ($PDE_4$) and, consequently, demonstrate their effectiveness for treating inflammatory diseases is shown by the following in vitro assay.

BIOLOGICAL ASSAY

Human Eosinophil $PDE_4$

Human peripheral blood is collected in ethylenediaminetetraacetic acid, diluted 1:2 in piperazine-N,N'-bis-2-ethanesulfonic acid (PIPES) buffer and then layered over percoll solution. Gradients are formed by centrifugation for 30 minutes at 2000 rpm at 4° C. The remainder of the isolation procedure, which is based on the procedure of Kita et al., J. Immunol., 152, 5457 (1994), is carried out at 4° C. The neutrophil/eosinophil layer is collected from the percoll gradient and the red blood cells are lysed. Remaining cells are washed in PIPES (1% FCS), incubated with anti-CD16 microbeads (MACS) for 1 hour, and passed over a magnetic column to remove the neutrophils. Eosinophils are collected in the eluate and analyzed for viability by trypan blue and purity by diff-quick stain. Eosinophil purity is routinely greater than 99% using this method.

Purified eosinophils are resuspended in 750 $\mu$L of PDE lysis buffer (20 mM triethylamine, 1 mM ethylenediaminetetraacetic acid, 100 $\mu$g/ml bacitracin, 2 mM benzamidine, 50 $\mu$M leupeptin, 50 $\mu$M PMSF, 100 $\mu$g/ml soybean trypsin inhibitor) and quick frozen in liquid nitrogen. Cells are thawed slowly and sonicated. Membranes are vortexed (disruption is confirmed by Trypan blue staining of fragments). Disrupted cells are centrifuged at 45 k rpm for 30 minutes at 4° C. to isolate membranes. Cytosol is decanted, and membrane resuspended to 200 $\mu$g/ml for use as PDE source in the hydrolysis assay yielding a window from 3000 to 5000 counts.

Compounds are dissolved in dimethyl sulfoxide at 10−2M, then diluted 1:25 in water to $4 \times 10^{-4}$ M. This suspension is serially diluted 1:10 in 4% dimethyl sulfoxide, for a final dimethyl sulfoxide concentration in the assay of 1%.

PHOSPHODIESTERASE INHIBITION ASSAY

To 12×75 mm glass tubes add:

25 $\mu$l PDE assay buffer (200 mM Tris/40 mM MgC12)

25 $\mu$l 4 nM/ml cAMP stock

25 μl test compound
25 μl PDE source (membrane)
Background control=membrane boiled 10'
Positive control=25 μl unboiled membrane
Incubate 25 minutes in 37° C. water bath.

Reaction is stopped by boiling samples 5 minutes. Samples are applied to Affigel column (1 ml bed volume) previously equilibrated with 0.25 M acetic acid followed by 0.1 mM N-[2-hydroxyethyl]piperazine-N'-2-ethanesulfonic acid (HEPES)/0.1 mM NaCl wash buffer (pH 8.5). cAMP is washed off column with HEPES/NaCl, 5'-AMP is eluted in 4 ml volumes with 0.25 M acetic acid. 1 ml of eluate is counted in 3 ml scintillation fluid for 1 minute ([3H].

Substrate conversion=(cpm positive control×4)/total activity. Conversion rate must be between 3 and 15% for experiment to be valid.

% Inhibition=1-(eluted cpm−background cpm/control cpm−bkgd cpm)×100.

$IC_{50}$s are generated by linear regression of inhibition titer curve (linear portion); and are expressed in μM.

TNF

The ability of the compounds or the pharmaceutically acceptable salts thereof to inhibit the production of TNF and, consequently, demonstrate their effectiveness for treating diseases Involving the production of TNF is shown by the following in vitro assay:

Peripheral blood (100 mls) from human volunteers is collected in ethylenediaminetetraacetic acid (EDTA). Mononuclear cells are isolated by Ficoll/Hypaque and washed three times in incomplete Hanks' balanced salt solution (HBSS). Cells are resuspended in a final concentration of $1 \times 10^6$ cells per ml in pre-warmed RPMI (containing 5% FCS, glutamine, pen/step and nystatin). Monocytes are plated as $1 \times 10^6$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10 μl) are then added to the cells at 3–4 concentrations each and incubated for 1 hour. Lipopolysaccharide (LPS) (10 μl) is added to appropriate wells. Plates are incubated overnight (18 hrs) at 37° C. At the end of the incubation period TNF was analyzed by a sandwich ELISA (R&D Quantikine lit). $IC_{50}$ determinations are made for each compound based on linear regression analysis.

Pharmaceutically-acceptable acid addition salts of the compounds of this invention include, but are not limited to, those formed with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic and succinic acid. Pharmaceutically-acceptable cationic salts of the compounds of this invention of formula I wherein $R^5$ is $CO_2R^6$ and $R^6$ is hydrogen include, but are not limited to, those of sodium, potassium, calcium, magnesium, ammonium, N,N'-dibenzylethylenediamine, N-methylglucamine (meglumine), ethanolamine and diethanolamine.

For administration to humans in the curative or prophylactic treatment of inflammatory diseases, oral dosages of the compounds of formula I and the pharmaceutically acceptable salts thereof (hereinafter also referred to as the active compounds of the present invention) are generally in the range of from 0.1–400 mg daily for an average adult patient (70 kg). Thus for a typical adult patient, individual tablets or capsules contain from 0.1 to 50 mg of active compound, in a suitable pharmaceutically acceptable vehicle or carrier. Dosages for intravenous administration are typically within the range of 0.1 to 40 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For administration to humans for the inhibition of TNF, a variety of conventional routes may be used including orally, parenterally and topically. In general, the active compound will be administered orally or parenterally at dosages between about 0.1 and 25 mg/kg body weight of the subject to be treated per day, preferably from about 0.3 to 5 mg/kg. The compound of formula I can also be administered topically in an ointment or cream in concentrations of about 0.5% to about 1%, generally applied 2 or 3 times per day to the affected area. However, some variation in dosage will necessarily occur depending on the condition of the subject being treated. The person responsible for administration will, in any event, determine the appropriate dose for the individual subject.

For human use, the active compounds of the present invention can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic.

The present invention is illustrated by the following examples, but it is not limited to the details thereof. The starting materials used in Preparations 1–4 are prepared ase described in PCT Publication WO 95/01980.

PREPARATION 1

1-Cyclopentyl-4,5-dihydro-3-ethyl-7-methylthio-1H-pyrazolo[3,4-c]pyridine

A magnetically stirred mixture of 1-cyclopentyl-3-ethyl-7-thio-4,5,6,7-tetrahydro-1H-pyrazolo[3,4c-]pyridine (0.322 grams), neutral silica gel (10 grams) and ether (100 ml) in a 500 ml erlenmeyer flask was cooled to 0° C. To this mixture was slowly added an excess solution of diazomethane in ether. Evolution of gas occurred and after 1 hour the reaction was quenched with acetic acid (1 drop), filtered and concentrated under reduced pressure to give a yellow oil. The oil was purified by chromatography on a silica gel column using 1:4 ethyl acetate/hexane as eluent to give 0.232 grams of a yellow oil. Anal. calcd. for $C_{14}H_{21}N_3S$: C, 63.85; H, 8.04; N, 15.94. Found: C, 64,01; H, 8.37; N, 15.71.

PREPARATION 2

1-Cyclopentyl-3-ethyl-7-thio-4,5,6,7-tetrahydro-1H-pyrazolo[3,4-c]pyridine

A solution of 1-cyclopentyl-3-ethyl-7-oxo-4,5,6,7-tetrahydro-1H-pyrazolo[3,4-c]pyridine (10.0 grams) in anhydrous 1,4-dioxane was treated with phosphorus pentasulfide (3.9 grams). After stirring at reflux for 12 hours the mixture was cooled to ambient temperature and concentrated under reduced pressure. The resulting yellow oil was dissolved in methylene chloride and washed with water and brine, dried over sodium sulfate and concentrated under reduced pressure. The orange residue was purified by chromatography on a silica gel column using a gradient mixture of hexanes in methylene chloride as eluent to give 9.3 grams of a yellow solid. Melting Point 152–3° C.; Anal. calcd. for $C_{13}H_{19}N_3S$: C, 62.63; H, 7.68; N, 16.86. Found: C, 62.14; H, 7.51; N, 16.35.

PREPARATION 3

1-cyclopentyl-3-ethyl-6(4-methoxyphenyl)-7-oxo-4, 5,6,7-tetrahydro-1-H-pyrazolo[3,4-c]pyridine A stirred mixture of 3-methoxy-1-(3-methoxyphenyl)-2-oxo-4-propionyl-1,2,5,6-tetrahydro-pyridine (0.49 grams, 1.7 mmole), cyclopentylhydrazine hydrochloride (0.40 grams) and sodium methoxide (46 mg, 0.85 mmole) in anhydrous ethanol was heated to reflux. After 16 hours, the mixture was concentrated under reduced pressure and chromatographed on a silica gel column using 1:4 ethyl acetate/hexane as eluent to give a white solid. Recrystallization from ether gave white needles. M.P. 64 . 65° C.; MS m/z [M+] 340.2025; HRMS [M+] 340.2046.

PREPARATION 4

1-Cyclopentyl-3-ethyl-7-oxo-4,5,6,7-tetrahydro-1H-pyrazolo[3,4-c]pyridine

A stirred solution of 1-cyclopentyl-3-ethyl-6-(4-methoxyphenyl)-7-oxo-4,5,6,7-tetrahydro-1H-pyrazolo[3, 4c]pyridine (2.58 grams, 7.60 mmoles) in acetonitrile (90 ml) at 0° C. is treated with a solution of ceric ammonium nitrate (12.5 grams, 22.8 mmoles) in water (110 ml). After stirring for 35 minutes the mixture is diluted with water (550 ml) and extracted with ethyl acetate (100 ml×4). The combined organics are washed with 50% saturated sodium bicarbonate (250 ml) followed by 10% sodium sulfite until the aqueous wash becomes pale yellow. The organic layer is then washed further with saturated bicarbonate and brine, and treated with decolorizing charcoal. After stirring for 30 minutes the mixture is dried over sodium sulfate, filtered through celite and concentrated under reduced pressure. The brown residue is recrystallized from ether to give 0.814 grams of a tan solid. M.P. 143–145° C.; MS (M/Z) 234; $^1$H NMR (250 MHz, CDCl$_3$) 1.21 (t, J=7.6 Hz, 3H), 1.62–2.13 (m, 8H), 2.62 (q, J=7.6 Hz, 2H) 2.73 (t, J=6.8 Hz, 2H), 3.51 (dt, J=2.7 and 6.8 Hz, 2H), 5.47 (s, 1H), 5.61 (pentet, J=1H).

EXAMPLE 1

9-Cyclopentyl-5,6-dihydro-7-ethyl-3-(3-pyridyl)-9H-pyrazolo[3,4-c]-1,2,4-triazolo[4,3-α]pyridine 1-Cyclopentyl-4,5-dihydro-3-ethyl-7-methylthio-1H-pyrazolo[3,4-c]pyridine (0.036 grams, 0.14 mmoles) and nicotinic acid hydrazide (0.021 grams, 0.15 mmoles) was dissolved in anhydrous pyridine (5 ml) in a flame dried flask. An oven-dried condenser was added, which was septa sealed and had an outlet to a bubbler. A long stainless steel needle was pierced through the septa and condenser center into the magnetically stirred solution. Nitrogen was bubbled through the long needle. The flask was heated to 135° C. for 4 hours. The pyridine was then removed under nitrogen purge. The resulting oil was heated to 150° C. for 4 hours. The flask was cooled to ambient temperature and contained 0.045 grams of the crude title compound as a white solid. The crude product did not contain any impurities measurable by thin layer chromatography. The product can be purified by either column chromatography on a silica gel column using a gradient mixture of ethyl acetate/hexane as eluent or by recrystallization from a mixture of ethyl acetate in hexane. Melting Point 140–5° C. (crude); $^1$H NMR (300 MHz, CDCl$_3$) δ 1.24 (t, J=7.6 Hz, 3H), 1.72 (m, 2H), 1.94 (m, 2H) 2.16 (m, 4H), 2.66 (q, J=7.6 Hz, 2H), 2.98 (t, J=7.0 Hz, 2H), 4.25 (t, J=7.0 Hz, 2H), 5.60 (quintet, J=7.7 Hz, 1H), 7.48 (dd, J=4.9 and 7.8 Hz, 1H), 8.05 (d, J=8.0 Hz, 1H), 8.75 (dd, J=1.4 and 4.9 Hz, 1H), 8.9 (d, J=1.7 Hz, 1H); Anal. calcd. for $C_{19}H_{22}N_6$: C, 68.23; H, 6.63; N, 25.13. Found: C, 67.39; H, 6.87; N, 24.00.

EXAMPLES 2–18

Reaction of the appropriate hydrazide with 1-cyclopentyl-4,5-dihydro-3-ethyl-7-methylthio-1H-pyrazolo[3,4-]pyridine, analogous to the procedure of Example 1, affords the following compounds of formula I wherein $R^1$ is ethyl and $R^3$ is cyclopentyl.

| Ex. # | $R^2$ | MP ° C. | MW | HRMS or Analysis (calcd.) %C, %H, %N | HRMS or Analysis (found) %C, %H, %N |
|---|---|---|---|---|---|
| 2 | phenyl | — | 333.42 | [M + H] 334.2032 | HRMS [M + H] 334.2032 |
| 3 | 2-furanyl | 95–97 | 323.43 | 66.85, 6.55, 21.67 | 67.29, 7.13, 19.56 |
| 4 | 3-methoxyphenyl | 130–2 | 363.45 | 69.39, 6.93, 19.27 | 69.42, 7.30, 18.13 |
| 5 | 3-thenyl | 134–5 | 353.5 | 64.55, 6.56, 19.81 | 64.62, 6.67, 18.57 |
| 6 | 2-methylphenyl | 109–12 | 347.45 | 72.59, 7.25, 20.16 | 71.40, 7.38, 19.49 |
| 7 | 2-methoxyphenyl | 132–7 | 363.47 | 69.39, 6.93, 19.27 | 68.61, 6.82, 18.82 |
| 8 | 4-hydroxyphenyl | 251–3 | 349.44 | 68.74, 6.63, 20.04 | 66.86, 6.69, 19.47 |
| 9 | 3-chloro-4-methylthien-2-yl | 136–8 | 387.94 | 58.82, 5.72, 18.05 | 58.54, 5.93, 17.88 |
| 10 | 5-(3-methyl pyrazole) | 305–6 | 337.43 | [M + H] 338.2093 | HRMS [M + H] 338.2093 |
| 11 | benzyl | 116–7 | 347.47 | [M + H] 347.2110 | HRMS [M + H] 347.2109 |
| 12 | 3-hydroxy phenyl | 240–3 | 349.45 | [M + H] 350.1981 | HRMS [M + H] 350.1981 |
| 13 | 2-hydroxy-3-methylphenyl | 147–9 | 363.47 | [M + H] 364.2137 | HRMS [M + H] 364.2137 |
| 14 | 2-hydroxy phenyl | 209 | 349.45 | 68.33, 6.66, 20.11 | 68.68, 6.63, 20.04 |
| 15 | 2-pyridyl | 153–5 | 334.43 | | MS (m/z) 335 |
| 16 | α-hydroxy benzyl | oil | 363.50 | | MS (m/z) 364 |
| 17 | 3,4-dimethoxy benzyl | 110–7 | 407.52 | [M + H] 408.2400 | HRMS [M + H] 408.2399 |
| 18 | 4-pyridyl | 198–200 | 334.39 | [M + H] 335.1984 | HRMS [M + H] 335.1984 |

EXAMPLE 19

9-Cyclopentyl-5,6-dihydro-7-ethyl-3-(thien-2-yl)-
9H-pyrazolo[3,4-c]-1,2,4-triazolo[4,3-α]pyridine 1-Cyclopentyl-3-ethyl-7-thio-4,5,6,7-tetrahydro-1H-pyrazolo[3,4-c]pyridine (0.35 grams, 1.4 mmole) was dissolved in 4 ml anhydrous pyridine in a flame dried flask under nitrogen. The flask was warmed to 70° C. and 1.5 ml of anhydrous hydrazine was added. The yellow solution turned pink and was stirred for 5 minutes. The pyridine and excess hydrazine were then removed under reduced pressure to give a pink solid that turned light green after being placed under vacuum (approximately 0.1 mm) for 30 minutes. Next, anhydrous pyridine (4 ml) followed by 2-thiophene carbonyl chloride (0.69 grams, 4.7 mmoles) was added to the flask and the mixture was stirred for 2 hours. The pyridine was removed under reduced pressure, and the residue was dissolved in dimethylformamide (4 ml) and heated at reflux for 2 hours. The mixture was then cooled to ambient temperature, diluted with water and extracted with ethyl acetate. The aqueous layer was basified to pH=12 with 1 N sodium hydroxide and extracted with ethyl acetate three times. The combined organics were washed with 1 N sodium hydroxide, water and brine, dried over sodium sulfate and concentrated under reduced pressure. The resulting oil was purified by chromatography on a silica gel column using a gradient mixture of ethyl acetate and hexane as eluent to give 304 mg of the title compound as a white solid. Melting Point 125–6° C.; $^1$H NMR (300 MHz, CDCl$_3$) δ 1.25 (t, J=7.5 Hz, 3H), 1.60–1.74 (m, 2H), 1.9–2.0 (m, 2H), 2.11–2.21 (m, 4H) 2.67 (q, J=7.6 Hz, 2H), 3.00 (t, J=7.1 Hz, 2H), 4.30 (t, J=7.1 Hz, 2H), 5.60 (quintet, J=7.7 Hz, 1H), 7.20 (dd, J=3.9 and 5.1 Hz, 1H), 7.49–7.54 (m, 2H); Anal. calcd. for C$_{18}$H$_{21}$N$_5$S: C, 63.68; H, 6.24, N, 20.63. Found: C, 63.66; H, 6.19; N, 21.00.

EXAMPLES 20–30

Reaction of the appropriate acid chloride with hydrazine and 1-cyclopentyl-3-ethyl-7-thio-4,5,6,7-tetrahydro-1H-pyrazolo[3,4-c]pyridine, analogous to the procedure of Example 19, affords the following compounds of formula I wherein R$^1$ is ethyl and R$^3$ is cyclopentyl.

70° C. Anhydrous hydrazine (2 ml) was added and the resulting yellow solution slowly turned beige. After 5 minutes the volatile materials were removed under reduced pressure to give a yellow solid. Next, anhydrous pyridine (5 ml) was added followed by 1-methyl cyclohexane carbonyl chloride (0.2 grams). After stirring for 2 hours at ambient temperature the pyridine was removed under reduced pressure and the residue was dissolved in dimethylformamide (5 ml). After stirring at reflux for 12 hours the solution was cooled to ambient temperature, diluted with water and extracted with ethyl acetate. The combined organics were washed with water and brine, and then dried over sodium sulfate. Concentration under reduced pressure gave a light brown oil. The oil was purified by chromatography on a silica gel column using 1:2 ethyl acetate/hexane as eluent to give 0.09 grams of a pale yellow solid. Melting Point 60–61° C.; MS (m/z) 380.

We claim:
1. A compound of the formula

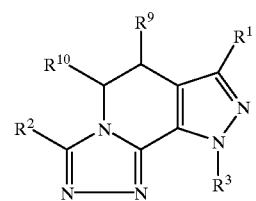

and the pharmaceutically acceptable salts thereof; wherein
R$^1$ is hydrogen, (C$_1$–C$_6$)alkyl, (C$_1$–C$_6$)alkoxy, (C$_2$–C$_4$) alkenyl, phenyl, dimethylamino, (C$_3$–C$_6$) cycloalkyl, (C$_3$–C$_6$)cycloalkyl(C$_1$–C$_3$)alkyl or (C$_1$–C$_6$)acyl wherein the alkyl, phenyl or alkenyl groups may optionally be substituted with up to two hydroxy, (C$_1$–C$_3$)alkyl, or trifluoromethyl groups, or up to three halogens;

R$^2$ and R$^3$ are each independently selected from the group consisting of hydrogen, (C$_1$–C$_{14}$)alkyl, (C$_1$–C$_7$)alkoxy (C$_1$–C$_7$)alkyl, (C$_2$–C$_{14}$)alkenyl, (C$_3$–C$_7$)cycloalkyl, (C$_3$–C$_7$)cycloalkyl(C$_1$–C$_2$)alkyl, a saturated or unsaturated (C$_4$–C$_7$)heterocyclic(CH$_2$)$_n$ group wherein n is

| Ex. # | R$^2$ | MP ° C. | MW | HRMS or Analysis (calcd.) %C, %H, %N | HRMS or Analysis (found) %C, %H, %N |
|---|---|---|---|---|---|
| 20 | n-propyl | 88–92 | 299.41 | [M + H] 300.2188 | HRMS [M+H] 300.2188 |
| 21 | methyl | 174–5 | 271–37 | 66.39, 7.80, 25.81 | 66.56, 7.85, 25.44 |
| 22 | 2-chlorophenyl | 132–4 | 367.89 | 65.29, 6.03, 19.05 | 65.24, 6.42, 18.83 |
| 23 | 3-chlorophenyl | 158 | 367.89 | 65.29, 6.03, 19.04 | 65.26, 6.37, 19.03 |
| 24 | cyclopentyl | oily | 325.48 | [M + H] 326.2345 | HRMS [M + H] 326.2345 |
| 25 | isopropyl | oily | 299.44 | | MS (m/z) 300 |
| 26 | 1-methylcyclohex-1-yl | oily | 353.4 | [M + H] 354.2658 | HRMS [M + H] 354.2658 |
| 27 | 2-chloropyrid-3-yl | 161–3 | 368.87 | 61.86, 5.74, 22.79 | 61.90, 5.94, 23.05 |
| 28 | 2-iodophenyl | 145–7 | 459.34 | 52.29, 4.83, 15.25 | 51.64, 5.00, 14.89 |
| 29 | 2-trifluoromethyl phenyl | 154–5 | 401.44 | 62.83, 5.53, 17.45 | 61.43, 5.53, 16.74 |
| 30 | tert-butyl | 144–5 | 313.45 | 68.97, 8.68, 22.34 | 68.60, 8.88, 22.51 |

EXAMPLE 31

5,6-dihydro-7-ethyl-9-(4-fluorophenyl)-3-(1-methylcyclohex-1-yl)-9H-pyrazolo[3,4-c]-1,2,4-triazolo[4,3-α]pyridine 3Ethyl-1(4-fluorophenyl)-7-thio-4,5,6,7-tetrahydro-1H-pyrazolo[3,4-c]pyridine (0.092 grams) was dissolved in anhydrous pyridine (5 ml) and the solution was warmed to 0, 1 or 2, containing as the heteroatom one or two of the group consisting of oxygen, sulphur, sulphonyl, nitrogen and NR$^4$ wherein R$^4$ is hydrogen or (C$_1$–C$_4$)alkyl; or a group of the formula

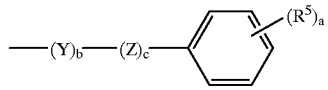

II wherein a is an integer from 1 to 5; b and c are 0 or 1; $R^5$ is hydrogen, hydroxy, $(C_1-C_5)$alkyl, $(C_2-C_5)$alkenyl, $(C_1-C_5)$ alkoxy, $(C_3-C_6)$cycloalkoxy, halogen, trifluoromethyl, $CO_2R^6$, $CONR^6R^7$, $NR^6R^7$, $NO_2$ or $SO_2NR^6R^7$ wherein $R^6$ and $R^7$ are each independently hydrogen or $(C_1-C_4)$alkyl; wherein Z is oxygen, sulphur, $SO_2$, CO or $NR^8$ wherein $R^8$ is hydrogen or $(C_1-C_4)$alkyl; and Y is $(C_1-C_5)$alkylene or $(C_2-C_6)$alkenyl optionally substituted with up to two $(C_1-C_7)$alkyl or $(C_3-C_7)$ cycloalkyl groups; wherein each of the alkyl, alkenyl, cycloalkyl, alkoxyalkyl or heterocyclic groups may optionally be substituted with one to fourteen of the group consisting of $(C_1-C_2)$alkyl, trifluoromethyl or halogen; and $R^9$ and $R^{10}$ are each independently selected from the group consisting of hydrogen, $(C_1-C_6)$alkyl, $(C_1-C_6)$ alkoxy, $(C_6-C_{10})$aryl and $(C_6-C_{10})$aryloxy.

2. A compound according to claim 1, wherein $R^1$ is methyl, ethyl or isopropyl.

3. A compound according to claim 1, wherein $R^3$ is $(C_1-C_6)$alkyl, $(C_2-C_6)$alkenyl, $(C_3-C_7)$cycloalkyl, $(C_3-C_7)$ cycloalkyl$(C_1-C_2)$allkyl or phenyl optionally substituted with 1 or 2 substituents selected from the group consisting of hydrogen, hydroxy, $(C_1-C_5)$alkyl, $(C_2-C_5)$alkenyl, $(C_1-C_5)$alkoxy, halogen, trifluoromethyl, $CO_2R^6$, $CONR^6R^7$, $NR^6R^7$, $NO_2$ and $SO_2NR^6R^7$ wherein $R^6$ and $R^7$ are each independently hydrogen or $(C_1-C_4)$alkyl.

4. A compound according to claim 1 selected from the group consisting of:

9-cyclopentyl-5,6-dihydro-7-ethyl-3-phenyl-9H-pyrazolo[3,4-c]-1,2,4-triazolo[4,3-α]pyridine;

9-cyclopentyl-5,6-dihydro-7-ethyl-3-(4-pyridyl)-9H-pyrazolo[3,4-c]-1,2,4-triazolo[4,3-α]pyridine;

9-cyclopentyl-5,6-dihydro-7-ethyl-3-(3-thenyl)-9H-pyrazolo[3,4c-]-1,2,4triazolo[4,3-α]pyridine;

3,9-dicyclopentyl-5,6-dihydro-7-ethyl-9H-pyrazolo[3,4c]-1,2,4-triazolo[4,3-α]pyridine;

9-cyclopentyl-5,6-dihydro-7-ethyl-3-(1-methylcyclohex-1-yl)-9H-pyrazolo[3,4-c]-1,2,4-triazolo[4,3-α] pyridine;

3-(tert-butyl)-9-cyclopentyl-5,6-dihydro-7-ethyl-9H-pyrazolo[3,4-c]-1,2,4-triazolo[4,3-α]pyridine;

9-cyclopentyl-5,6-dihydro-7-ethyl-3-(thien-2-yl)-9H-pyrazolo[3,4-c]1,2,4-triazolo[4,3-α]pyridine;

3-(2-chlorophenyl)-9-cyclopentyl-5,6-dihydro-7-ethyl-9H-pyrazolo[3,4-c]-1,2,4-triazolo[4,3-α]pyridine;

9-cyclopentyl-5,6-dihydro-7-ethyl-3-(2-iodophenyl)-9H-pyrazolo[3,4c]-1,2,4-triazolo[4,3-α]pyridine; and 5,6-dihydro-7-ethyl-9-(4-fluorophenyl)-3-(1-methylcyclohex-1-yl)-9H-pyrazolo[3,4-c]-1,2,4-triazolo[4,3-α]pyridine.

5. A method for the inhibition of phosphodiesterase (PDE) type IV and the production of tumor necrosis factor (TNF) in a patient in need thereof comprising administering to said patient a phosphodiesterase type IV inhibiting and tumor necrosis factor production inhibiting amount of a compound according to claim 1.

6. A method of treating an inflammatory condition in a mammal in need thereof which comprises administering to said mammal an antiinflammatory amount of a compound of the formula I or a pharmaceutically acceptable salt thereof.

7. A method of treating a disease or condition selected from the group consisting of asthma, bronchitis, chronic obstructive airway disease, allergic rhinitis, and dermatitis, comprising administering to a patient in need of such treatment a therapeutically effective amount of a compound according to claim 1.

\* \* \* \* \*